(12) United States Patent
Nord et al.

(10) Patent No.: US 7,986,768 B2
(45) Date of Patent: Jul. 26, 2011

(54) APPARATUS AND METHOD TO FACILITATE GENERATING A TREATMENT PLAN FOR IRRADIATING A PATIENT'S TREATMENT VOLUME

(75) Inventors: Janne Nord, Espoo (FI); Antti Viitala, Helsinki (FI)

(73) Assignee: Varian Medical Systems International AG, Zug (CH)

( * ) Notice: Subject to any disclaimer, the term of this patent is extended or adjusted under 35 U.S.C. 154(b) by 0 days.

(21) Appl. No.: 12/389,051

(22) Filed: Feb. 19, 2009

(65) Prior Publication Data

US 2010/0208867 A1 Aug. 19, 2010

(51) Int. Cl.
*A61N 5/10* (2006.01)
(52) U.S. Cl. ........................ 378/65
(58) Field of Classification Search .......... 378/65
See application file for complete search history.

(56) References Cited

U.S. PATENT DOCUMENTS

| | | | |
|---|---|---|---|
| 5,602,892 A | 2/1997 | Llacer | |
| 5,782,739 A | 7/1998 | Criss et al. | |
| 6,038,283 A | 3/2000 | Carol et al. | |
| 6,260,005 B1 | 7/2001 | Yang et al. | |
| 6,411,675 B1 | 6/2002 | Llacer | |
| 6,560,311 B1 | 5/2003 | Shepard et al. | |
| 6,661,870 B2 * | 12/2003 | Kapatoes et al. | 378/65 |
| 6,882,702 B2 | 4/2005 | Luo | |
| 7,162,008 B2 | 1/2007 | Earl et al. | 378/65 |
| 7,180,980 B2 | 2/2007 | Nguyen | |
| 7,333,591 B2 | 2/2008 | Earl et al. | 378/65 |
| 2003/0048868 A1 | 3/2003 | Bailey et al. | |
| 2005/0201516 A1 * | 9/2005 | Ruchala et al. | 378/65 |
| 2006/0078086 A1 | 4/2006 | Riley et al. | |
| 2006/0256915 A1 | 11/2006 | Otto et al. | 378/65 |
| 2008/0144772 A1 | 6/2008 | Yi et al. | 378/65 |
| 2008/0226030 A1 | 9/2008 | Otto | 378/65 |
| 2008/0298550 A1 | 12/2008 | Otto | 378/65 |

FOREIGN PATENT DOCUMENTS

| | | |
|---|---|---|
| WO | 03076003 A2 | 9/2003 |
| WO | 2005035061 A2 | 4/2005 |
| WO | 2008011725 A1 | 1/2008 |
| WO | 2008130634 A1 | 10/2008 |

OTHER PUBLICATIONS

Yi et al., "A Dose Rate Modulated Tracking Radiation Therapy System and Method," U.S. Appl. No. 60/874,678, filed Dec. 14, 2006; 23 pages.
Wang et al., "Arc-Modulated Radiation Therapy (AMRT): A Single Arc Form of Intensity-Modulated Arc Therapy," Physics in Medicine and Biology 53 (2008); 13 pages; IOP Publishing.

(Continued)

*Primary Examiner* — Courtney Thomas
(74) *Attorney, Agent, or Firm* — Fitch Even Tabin & Flannery

(57) ABSTRACT

One provides (101) a plurality of different treatment plans for a given patient, wherein at least one such plans is provided by using deformation information that is obtained by using historical information for persons other than the given patient regarding physical changes over time as correspond to at least one volume within the given patient and/or calculated information regarding physical changes as correspond to the at least one volume within the patient. Obtained data (102) as pertains to the patient is then used to select (103) a particular one of the aforementioned plurality of different treatment plans.

20 Claims, 2 Drawing Sheets

OTHER PUBLICATIONS

Search Report from Related PCT/EP2010/052156; dated May 5, 2010, 14 pages.

Xing et al., "Fast Iterative Algorithms for Three-Dimensional Inverse Treatment Planning," Medical Physics, Oct. 1998, pp. 1845-1849, vol. 25 (10); American Association of Physicists in Medicine, US, 5 pages.

Siebers et al., "Acceleration of dose calculations for intensity-modulated radiotherapy," Medical Physics, Jun. 2001, pp. 903-910, vol. 28 (6); American Association of Physicists in Medicine, US 8 pages.

Djajaputra et al., "Algorithms and performance of a clinical IMRT Beam-Angle Optimization System," Phy. Med. Bio. 2003; vol. 48, pp. 3191-3212.

* cited by examiner

US 7,986,768 B2

APPARATUS AND METHOD TO FACILITATE GENERATING A TREATMENT PLAN FOR IRRADIATING A PATIENT'S TREATMENT VOLUME

RELATED APPLICATION(S)

This application is related to co-pending and co-owned:

(A) U.S. patent application Ser. No. 11/954,638, entitled TREATMENT PLANNING SYSTEM AND METHOD FOR RADIOTHERAPY and filed Dec. 12, 2007; and (B) U.S. patent application Ser. No. 12/207,265, entitled METHOD AND APPARATUS TO FACILITATE ADAPTING AN IRRADIATION TREATMENT PLAN and filed Sep. 9, 2008;

which are incorporated by reference in their entirety herein (including specifically the various definitions and word/expression characterizations contained therein).

TECHNICAL FIELD

This invention relates generally to irradiation therapy treatment plans.

BACKGROUND

Radiation therapy techniques are known. Generally speaking, a trained person such as a radiologist treats a patient having undesired tissue (such as a tumor) by irradiating the undesired tissue in order to reduce or eradicate that undesired tissue. As such treatment can also damage or destroy healthy tissue, such radiation is typically administered in accordance with a corresponding plan. The goal of such a plan is usually to control the shape, strength, timing, and other characterizing attributes of the radiation beam (or beams) to limit the effects of the radiation to only the undesired tissue.

The development of such a plan comprises a complicated and often dynamic undertaking. Such a plan will ordinarily need to account for both the general geometries and characteristics of a given radiation platform as well as the unique attributes or capabilities of a given specific radiation platform to be employed in a given treatment scenario. Such a plan will also often heavily depend upon information regarding the undesired tissue itself as well as desired tissue in the treatment volume. This can include, for example, information concerning the treatment volume itself (such as the size and shape of the treatment volume) as well as relative positioning of that treatment volume with respect to other adjacent desired tissue.

As radiation therapy often plays out in numerous treatment sessions over an extended period of time, yet another related complication can arise; changes over time with respect to the absolute and relative locations of the undesired and desired tissues and/or changes to their relative geometry. Such changes can be owing, for example, to differences in elasticity of the various materials involved (for example, as they react to various stimuli such as the relative fullness or emptiness of a nearby organ such as the bladder), shrinkage (or growth) of these materials, and so forth.

Such changes are problematic because they create at any given moment a need for a treatment plan that is likely different than a treatment plan that was previously used with a given patient. The time-consuming nature of forming and approving such a plan to accommodate such changes, however, is highly inconsistent with the temporal needs of the patient and the treatment facility itself in most cases. Furthermore, such plans typically require the approval of one or more expert practitioners who are often not immediately available to offer their approvals on a schedule that matches the dynamic requirements of such a treatment facility.

BRIEF DESCRIPTION OF THE DRAWINGS

The above needs are at least partially met through provision of the method and apparatus to facilitate generating a treatment plan for irradiating a patient's treatment volume described in the following detailed description, particularly when studied in conjunction with the drawings, wherein.

Figure 1:
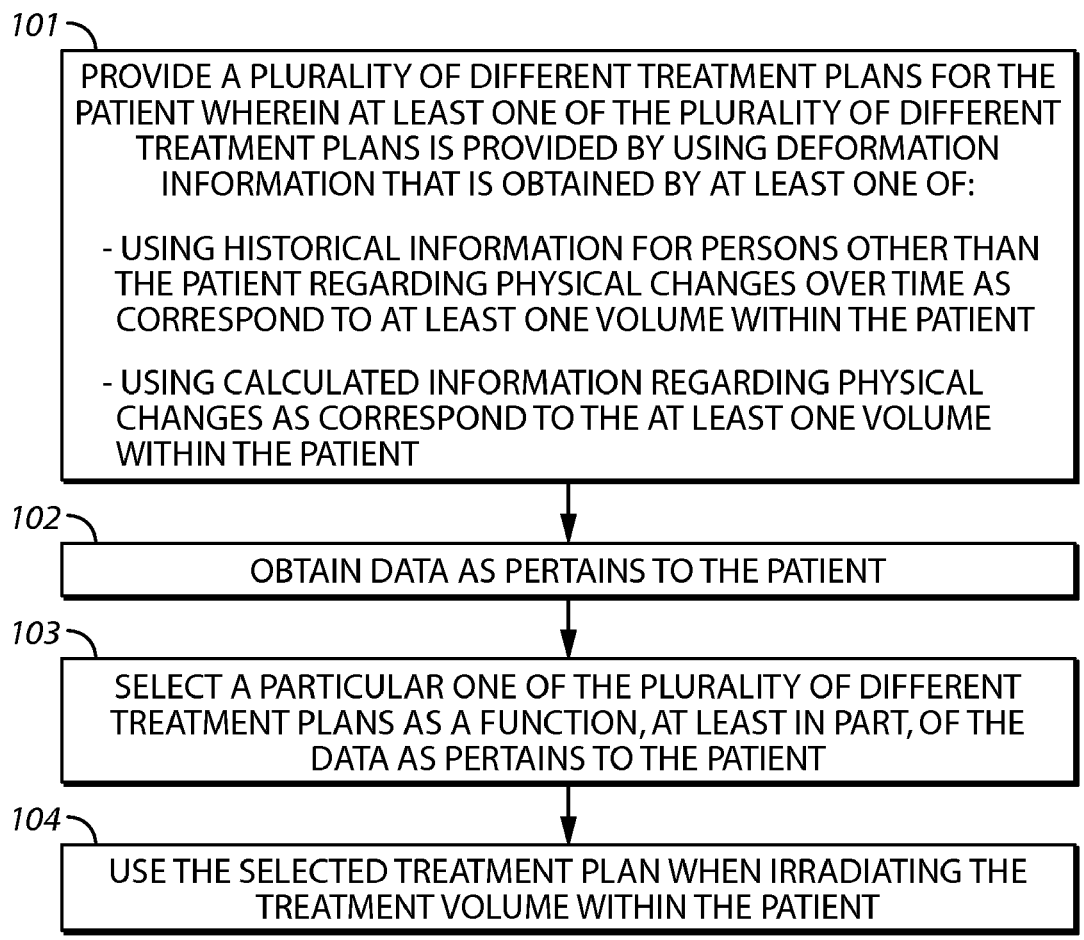
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments serve to facilitate the generation of a treatment plan (or plans) for irradiating a treatment volume within a patient. As used herein, it will be understood that this expression "treatment volume" refers to an area, typically but not necessarily fully subsumed within a patient's body, that may include (in whole or in part) one or more organs, tissues, glands, or the like where typically some of the included material comprises desired material and some of the included material comprises undesired material (where the latter usually comprises the target of the irradiation treatment).

Pursuant to these teachings, one provides a plurality of different treatment plans for a given patient. At least one of these treatment plans is provided by using deformation information that can be applied to modify an original diagnostic image as pertains to the treatment volume. The deformation information can comprise, for example, information regarding anticipated changes over time as are likely to apply with respect to the patient in question. By one approach one obtains this deformation information by using historical information for persons other than the given patient regarding physical changes over time as correspond to at least one volume within the given patient. This one volume, for example, can be identical to, or at least overlap in some respects with, the aforementioned treatment volume. This historical information can comprise, for example, information regarding changes to geometry as pertain to the at least one volume within the patient and/or information regarding movement of specific objects within that treatment volume.

By another approach, used in combination with the historical information described above or in lieu thereof, one obtains this deformation information by using calculated information regarding physical changes as correspond to the at least one volume within the patient. For example, this calculated information can comprise calculations based upon elasticity information for at least one object within the treatment volume. As another example in these regards, a clinical expert (or experts) might provide possible movement data for a limited set of points within the patient and other points within the patient could then be moved according to calculations that are based upon a corresponding elasticity model.

These teachings then provide generally for obtaining data as pertains to the patient and then selecting a particular one of the aforementioned plurality of different treatment plans as a function, at least in part, of this patient data. By one approach, for example, this can comprise selecting a particular one of the plurality of different treatment plans as corresponds to the modified image (that was formed through modification of an original diagnostic image as pertains to the treatment volume using the aforementioned deformation information) having at least one metric that correlates most closely to a corresponding metric in the data as pertains to the patient.

These teachings will then accommodate using the selected treatment plan when irradiating the treatment volume within the patient.

Those skilled in the art will appreciate that the step of providing the plurality of different treatment plans for a given patient can be undertaken well prior to the step of selecting a particular one of the plurality of treatment plans to be employed in a given treatment session. For example, at least some of these different treatment plans can be formed hours, days, or even weeks (or more) prior to the patient visiting the treatment facility for the administration of the selected plan. This means, of course, that the time requirements to formulate such plans, and gaining the approval of such treatment plans from skilled and authorized persons, can be readily accommodated in a way that is fully compatible with the time requirements of the treatment facility and the patient. Those skilled in the art will also recognize, of course, that these teachings can also be employed in a more immediate context (as when, for example, the patient is prepped and awaiting treatment).

These and other benefits accrue, at least in substantial part, to the use of the aforementioned historical and/or calculated information. In particular, the use of such information permits useful and likely-valid treatment plans to be developed for a given patient that account for likely physical alterations within that patient's treatment volume.

These and other benefits may become clearer upon making a thorough review and study of the following detailed description. Referring now to the drawings, and in particular to FIG. 1, an illustrative process that is compatible with many of these teachings will now be presented. As alluded to earlier, this process 100 serves to facilitate generating a treatment plan for irradiating a treatment volume within a patient.

This process 100 includes the step 101 of providing a plurality of different treatment plans for the patient. By one approach, this can comprise generating one or more of these different treatment plans in conjunction with the patient's visit to the treatment facility to receive a corresponding radiation treatment. By another (perhaps more useful and likely) approach, some or all of these treatment plans are generated well prior to a present need to select and implement such a plan. This can mean, for example, generating these plans days, weeks, or possibly even months prior to an immediate need for the availability of such plans.

This step 101 can comprise providing at least one of these different treatment plans by using deformation information obtained via at least one of two possible general approaches. By a first such approach, this can comprise using historical information for persons other than the patient. This historical information can itself comprise information regarding physical changes over time as correspond to at least one volume within the patient. In a typical application setting, this volume will coincide, at least in part, with the patient's anticipated or planned treatment volume. Those skilled in the art will recognize that at least some such physical changes are, for all intents and purposes, random changes. Accordingly, it will generally not be possible to accurately predict with certainty a particular all-encompassing view of the treatment volume.

One example in this regard would be information regarding changes to geometry as pertain to at least one volume within the patient. This can comprise, for example, a previously-treated treatment target that is expected to shrink in size during the course of treatment.

Another example of potentially useful historical information would be information regarding the movement of specific objects within the treatment volume. This can comprise, for example, an object such as a prostate gland that will move as the patient's bladder experiences different states of fullness.

As noted, this historical information includes information empirically developed from persons other than the patient. This does not preclude also using relevant historical information for this patient when and as available, but in a typical application setting such a fortuitous circumstance will usually be the exception rather than the rule. This historical information can be gleaned from any of a variety of sources including but not limited to medical studies and research of various kinds. This historical information can be as general, or as specific, as may be desired and/or as the source content may permit. For example, when and as appropriate, this historical information can be limited to information derived from persons having the same gender, age, height, weight, genetic predispositions, and/or the like as the patient.

By a second such approach, the deformation information for one or more of these different treatment plans can be obtained by using calculated information regarding physical changes as correspond to the at least one volume within the patient. Such calculations can be based upon any of a variety of potential parameters of interest. As one example in these regards, these calculations can be based upon elasticity information for at least one object within the treatment volume.

As used herein, this reference to "elasticity" should be taken broadly. By one approach, for example, this can refer to physical elasticity. For example, some objects in the body, such as the walls of the bladder, are considerably more physically elastic than other objects in the body, such as bone. Mathematically-modeled representations of such objects can serve to yield the aforementioned deformation information. By one approach, such elasticity can be accounted for via use of one or more corresponding elasticity models (where, for example, some or all of the contents of the elasticity model are calculated using Hounsfield unit values as derived from one or more patient images).

By another example, this reference to elasticity can be understood to refer to biological elasticity. A simple example of biological elasticity is that the amount of various gases, liquids, and/or solids present in various parts of the body (such as, for example, the amount of liquid material in a bladder, the amount of material in the digestive tract, the amount of air in the lungs, and so forth) can change over time. Another simple example of biological elasticity is sliding interfaces between various objects in the volume of interest. Those skilled in the art will recognize that such objects can comprise any of a variety of organs and other anatomical structures. As one non-limiting example of a sliding interface of interest is the ability of one organ or other structure to slide past another by translating in addition to rotating with respect to one another.

As noted, one or more of the aforementioned treatment plans can be provided by using deformation information that is itself obtained using such historical and/or calculated information. These teachings will readily accommodate a great number of permutations and combinations in these regards. For example, by one approach, only one of the treatment plans might be based only upon historical information with the remaining treatment plans having a different origin. As another example, only one of these treatment plans might be based only upon calculated information with the remaining treatment plans again having an origin other than via such historical or calculated information. As another example in these regards, one of the treatment plans may be derived from historical information, another of the treatment plans may be derived from calculated information, and all of the remaining plans based upon a different origin.

These teachings will also accommodate having a greater number of treatment plans based upon such information sources. For example, two (or more) of the treatment plans can be based upon historical information (or calculated information), up to and including all of the treatment plans. These teachings will also accommodate having some plans (from one to nearly all) based upon the historical information and some plans (from one to nearly all) based upon the calculated information.

Those skilled in the art will also appreciate that these teachings will further accommodate providing one or more treatment plans that are each based both upon the historical information and the calculated information.

By one approach, this step 101 of providing these differing treatment plans can include using the aforementioned deformation information to modify an original diagnostic image as pertains to the treatment volume to thereby provide at least one modified image. (As used herein, this reference to "original" will be understood to refer to a previously captured diagnostic image, such as an X-ray image, a CAT scan image, an MRI image, and so forth for the patient. This image may, or may not, be a first such image for this particular patient.)

Figure 2:
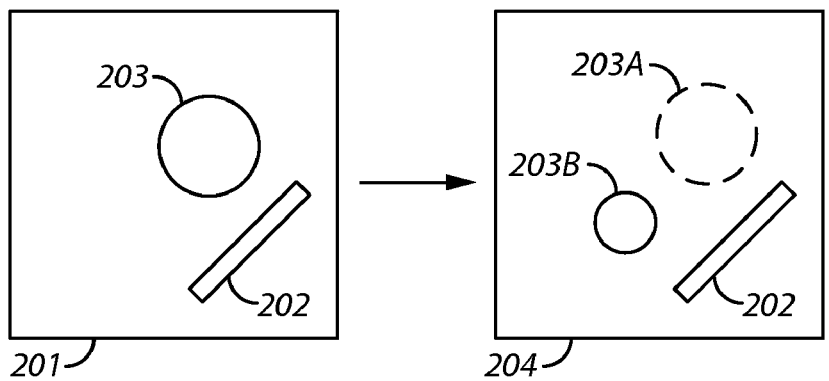
FIG. 2 comprises a schematic view as configured in accordance with various embodiments of the invention.

Referring momentarily to FIG. 2, and by way of illustration and without intending any limitations in these regards, an original diagnostic image 201 can include a first object 202 and a second object 203 that are both within the treatment volume of the patient. Using deformation information gleaned from the aforementioned historical information and/or calculated information, this original image 201 is modified in this example to provide a modified image 204 where the aforementioned second object 203 no longer has a same location or size (as denoted by the phantom line object denoted by reference numeral 203A) but has instead shrunken to a smaller size and moved to a different location as denoted by reference numeral 203B.

Those skilled in the art will understand that this modified image 204 is not wholly based upon current empirical information for the patient. Instead, an original image 201 for this patient is modified to incorporate historically-based and/or calculation-based deformation information. This modified image 204 may, or may not, conform closely to the patient's actual presentation at the time of treatment. Being based upon a reliable historical and/or calculated foundation, however, this modified image 204 presents a reasonable possibility in these regards.

It will therefore be understood that, in a typical application setting, these teachings will comprise providing a variety of different modified images that each present a possible scenario for how the patient will actual present himself or herself at the time of treatment. The number of such candidate images provided in a given instance can vary with the needs and/or opportunities as tend to characterize a given application setting. In some cases, for example, five to ten such modified images may suffice to adequately represent a useful range of possibilities for a given patient. In other cases, it may be more appropriate to provide twenty, thirty, or more such modified images while in yet other cases it may be adequate to simply provide for only one or two such modified images.

This step 101 of providing a plurality of different treatment plans can comprise developing a treatment plan that is specific and appropriate to each of these candidate modified images. These treatment plans can vary from one another, for example, with respect to various treatment equipment settings such as radiation intensity, time of exposure, directionality, and so forth. Each such plan can be fully developed using whatever plan-development process a given practitioner may prefer.

Each such plan can further be vetted and approved by such persons and via whatever authorization process a given service provider may deem necessary. Those skilled in the art will appreciate that the time requirements inherent to such activities are largely without adverse consequence to maintaining an ability to receive, treat, and dismiss a given patient in an efficient and timely manner because these activities can all be undertaken and concluded well in advance of a present need to implement a particular treatment plan for the patient.

Referring again to FIG. 1, this process 100 then provides for the step 102 of obtaining data as pertains to the patient. In a typical application setting this will comprise obtaining this information at a time that is just prior to administering the corresponding radiation treatment. As one non-limiting example in this regard, this patient data can be obtained within one hour of when the treatment is to be administered.

The precise nature of this data can of course vary with respect to the application setting, the patient, the nature of the treatment itself, and the native capabilities of the treatment facility. Generally speaking, however, in many cases this data can comprise image data that corresponds to the patient's treatment volume. Examples include, but are not limited to, x-ray images, computed tomography (CT) images, magnetic resonance imaging (MRI) images, ultrasound images, and so forth. In many cases this data can be captured, in the first instance, in a digital form. Those skilled in the art will recognize and appreciate that the following steps can also be carried out in a digital realm, hence leveraging the value of capturing the patient data in a digital form.

This process 100 then provides the step 103 of selecting a particular one of the aforementioned plurality of different treatment plans as a function, at least in part, of the aforementioned patient data to thereby provide a selected treatment plan. By one approach, for example, this can comprise selecting a particular one of the plurality of different treatment plans as corresponds to a given one of the aforementioned modified images that best matches an image as corresponds to aforementioned patient data. Such an approach can comprise, for example, identifying the modified image having at least one metric that correlates most closely to a corresponding metric in the data as pertains to the patient. Such a metric can comprise, for example, a location of the center of the tissue to be treated, a diameter or peripheral measurement for the tissue to be treated, a given distance from a center of the tissue to be treated from some other point of reference, a given distance as pertains to one or more marker seeds as were previously implanted within the treatment volume, an angle of rotation of an organ or structure, a volume of the contents contained within a given organ, a volume or other dimension of a given target object, and so forth. By way of further example (but not by way of limitation), this metric can comprise a metric regarding at least one of a change in tumor size, a change in organ volume, a change in patient weight, a change in patient structure position (where "structure" will be understood to comprise an organ or other body as comprises a physical part (including both biological (including various tissues, bones, and so forth) and non-biological parts) of the patient), a rotation of a patient structure, and a translation of a patient structure.

In many cases, of course, it will be useful to identify a particular modified image as best matching the patient's present data by referencing more than one such metric. By one approach, one or more computer-implemented pattern-matching algorithms of choice can be employed to perform, in whole or in part, this step 103. There are numerous such algorithms known in the art. This step 103 can also employ, in combination with the above or in lieu thereof, the use of implanted seeds as a basis for measurements of value in selecting a particular plan.

It will be further appreciated that this step 103 can also comprise selecting the particular one of the plurality of different treatment plans to use when treating the patient as a function, at least in part, of both the data as pertains to the patient as well as information regarding results of at least one previous treatment of the treatment volume. This might comprise, for example, using clinical test results from which one can estimate a relative size or position of a given object within the treatment volume. Such clinical test results might comprise, for example, certain blood test results or the like.

This process 100 then provides the follow-on step 104 of using the selected treatment plan when irradiating the treatment volume within the patient. This can of course comprise automatically or manually setting one or more operational settings for the treatment platform and/or physically positioning the patient in a particular way to comport with the specifications of the selected treatment plan.

Figure 3:
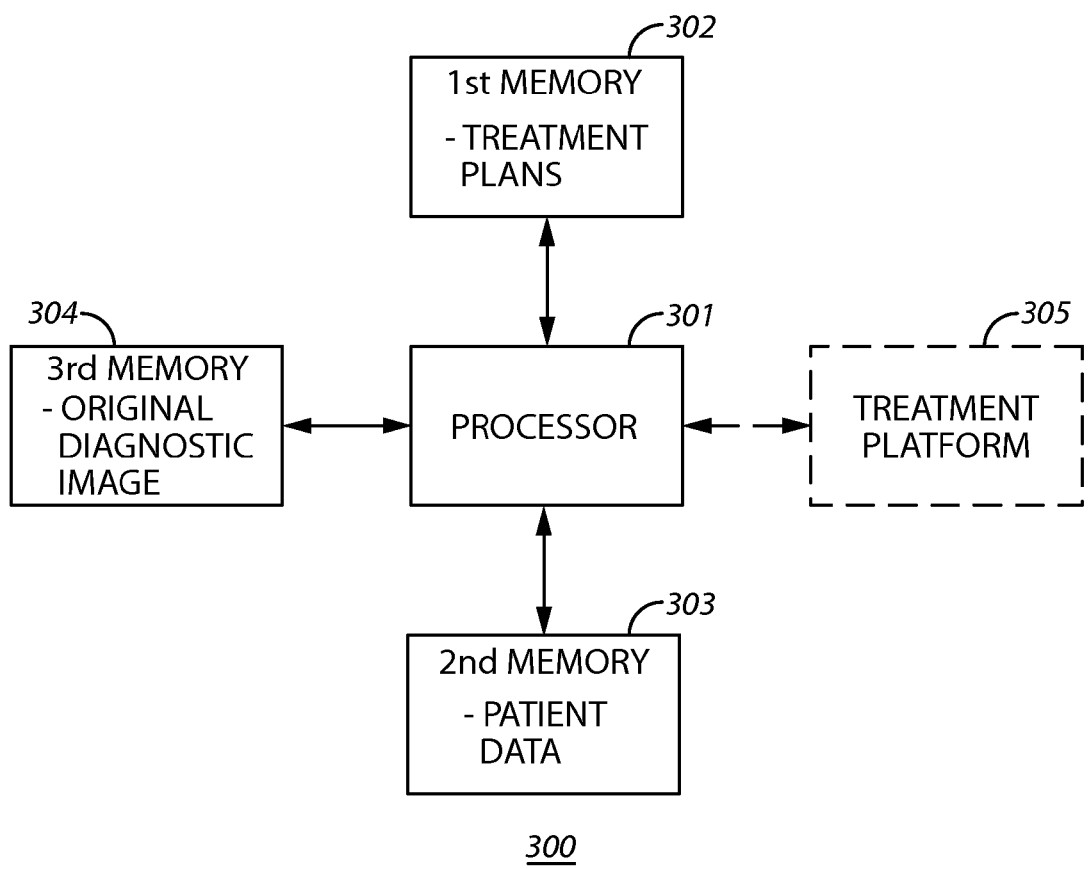
FIG. 3 comprises a block diagram as configured in accordance with various embodiments of the invention.

Those skilled in the art will appreciate that the above-described processes are readily enabled using any of a wide variety of available and/or readily configured platforms, including partially or wholly programmable platforms as are known in the art or dedicated purpose platforms as may be desired for some applications. Referring now to FIG. 3, an illustrative approach to such a platform will now be provided.

In this illustrative example, an apparatus 300 to facilitate generating a treatment plan for irradiating a treatment volume within a patient comprises a processor 301 that operably couples to a first memory 302, a second memory 303, and a third memory 304. Those skilled in the art will recognize and appreciate that such a processor 301 can comprise a fixed-purpose hard-wired platform or can comprise a partially or wholly programmable platform. All of these architectural options are well known and understood in the art and require no further description here.

The first memory 302 can have stored therein the aforementioned plurality of different treatment plans for the patient. It will be recalled that at least one of these treatment plans is provided through use of deformation information that is obtained through use of historical information for persons other than the patient, calculated information regarding physical changes as correspond to at least one volume within the patient, or both. The second memory 303 can have stored therein the aforementioned data as pertains to the patient. The third memory 304 can have stored therein the aforementioned original diagnostic image as pertains to the treatment volume. It will be understood that the memory components shown can comprise a plurality of memory elements (as is suggested by the illustration) or can be comprised of a single memory element. It will also be understood that these memory components can be local to the processor 301 or can be remotely located and accessed via an intervening network such as a local area network (LAN), the Internet, or the like.

The processor 301 can be configured (using, for example, corresponding programming as will be well understood by those skilled in the art) to carry out one or more of the steps, actions, or functionality set forth herein. This can comprise, for example, configuring the processor 301 to use the deformation information to modify the original diagnostic image as pertains to the treatment volume to thereby provide at least one corresponding modified image. This can further comprise, for example, using a user interface (not shown) to permit a user to select a particular one of the plurality of different treatment plans as corresponds to a modified image having at least one metric that correlates most closely to a corresponding metric in the data as pertains to the patient. In the alternative, the processor 301 can be configured to automatically make this determination itself. As yet another alternative, the processor 301 can be configured to identify one (or more) candidate modified images as best matching the patient's current data and to present that candidate modified image (or images) to a user of the apparatus 300 to gain their final selection and/or approval of the selection.

If desired, the details regarding this selection can then be passed, automatically or in response to an end user's instruction, to the treatment platform 305. This can comprise, by one approach, having the processor 301 automatically adjust one or more of the operating settings of the treatment platform. This can include, for example, setting radiation intensity levels, exposure durations, pulse rates, field shapes, energy, lateral intensity distribution, and so forth to match the specifications of the selected treatment plan.

Those skilled in the art will recognize and understand that such an apparatus 300 may be comprised of a plurality of physically distinct elements as is suggested by the illustration shown in FIG. 3. It is also possible, however, to view this illustration as comprising a logical view, in which case one or more of these elements can be enabled and realized via a shared platform. It would be possible, for example, to integrate the described functionality with the treatment platform 305 itself. It will also be understood that such a shared platform may comprise a wholly or at least partially programmable platform as are known in the art.

So configured, patients can be received and treated in a relatively short period of time in a manner that does not require an immediate and on-site presence of expert practitioners having the requisite knowledge, experience, and authorization to select a particular treatment plan for a given patient. Notwithstanding this high level of temporal efficiency, these teachings also tend to encourage and permit a high degree of personal customization of a treatment plan for a given patient. It will be appreciated that these teachings are highly compatible with existing treatment platforms and decision-making processes and hence are keenly capable of greatly leveraging such existing approaches. It will be further appreciated that these teachings are highly scalable and are suitable for use in a wide variety of application settings involving a wide variety of treatments, patients, and treatment volumes.

Those skilled in the art will also appreciate that these teachings can be applied to accommodate yet another category of clinical variations—day-to-day variations with respect to the patient's position and pose during the treatment process itself. Changes with respect to articulation of skeletal anatomy, for example, can produce significant changes to other body materials. Rotation of bony joints, for example, can and will distort affected soft tissues (consider, for example, that the angle of the two femurs in the pelvic girdle can and will cause significant distortion of the soft tissue anatomy in the pelvis). As another example in these regards, a simple rotation of the patient's head within a face mask will result in a shift in the location of the base of the skull; this, in turn, results in a shift of the curvature in the cervical spine. At least one or more of the various treatment plans of these teachings can be designed and selected to accommodate such variations with respect to the pose-based presentation of the patient to thereby further ease the patient's burden in these regards while nevertheless tending to assure the desired treatment of the patient's condition.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. As one example in these regards, these teachings will readily accommodate providing a plurality of treatment strategies that each represent some allowable random variations in the patient (as may relate, for example, to the variable fullness of the patient's bladder and so forth), which variations are applied to a baseline plan to yield the aforementioned treatment plans. As another example in these regards, these teachings will also readily accommodate anticipated and articulated drift in such a baseline plan (as may be appropriate in application settings where, for example, the clinical response to treatment over time can include a rapid change in size (as when tumors, such as certain tumors in the head or neck region may respond quickly to therapy by rapidly shrinking over time) or where healthy organs-at-risk are likely to move into a high dose region and become exposed to that corresponding risk). And it would also of course be possible to combine the use of a shifting baseline plan with the aforementioned variations-based modifications to a given baseline.

We claim:

1. A method to facilitate generating a treatment plan for irradiating a treatment volume within a patient, comprising:
   providing a plurality of different treatment plans for the patient wherein at least one of the plurality of different treatment plans is provided by using deformation information that is obtained by at least one of:
      using historical information for persons other than the patient regarding physical changes over time as correspond to at least one volume within the patient; and
      using calculated information regarding physical changes as correspond to the at least one volume within the patient, wherein the calculated information comprises at least elasticity information for at least one object within the treatment volume;
   obtaining data as pertains to the patient;
   selecting a particular one of the plurality of different treatment plans as a function, as least in part, of the data as pertains to the patient to provide a selected treatment plan;
   using the selected treatment plan when irradiating the treatment volume within the patient.

2. The method of claim 1 wherein at least one of the plurality of different treatment plans is provided by using the historical information for persons other than the patient regarding physical changes over time as correspond to the treatment volume and at least another of the plurality of different treatment plans is provided by using the calculated information regarding physical changes as correspond to the treatment volume.

3. The method of claim 1 wherein at least one of the plurality of different treatment plans is provided by using both the historical information for persons other than the patient regarding physical changes over time as correspond to the treatment volume and the calculated information regarding physical changes as correspond to the treatment volume.

4. The method of claim 1 wherein a plurality of the different treatment plans are provided by at least one of:
   using historical information for persons other than the patient regarding physical changes over time as correspond to the treatment volume; and
   using calculated information regarding physical changes as correspond to the treatment volume.

5. The method of claim 1 wherein the historical information comprises information regarding changes to geometry as pertain to the at least one volume within the patient.

6. The method of claim 1 wherein the historical information comprises information regarding movement of specific objects within the treatment volume.

7. The method of claim 1 further comprising:
   using the deformation information to modify an original diagnostic image as pertains to the treatment volume to thereby provide at least one modified image.

8. The method of claim 1 wherein selecting a particular one of the plurality of different treatment plans as a function, as least in part, of the data as pertains to the patient to provide a selected treatment plan comprises selecting a particular one of the plurality of different treatment plans as corresponds to a modified image having at least one metric that correlates most closely to a corresponding metric in the data as pertains to the patient.

9. The method of claim 8 wherein the corresponding metric in the data as pertains to the patient comprises a metric regarding at least one of a change in tumor size, a change in organ volume, a change in patient weight, a change in patient structure position, a rotation of a patient structure, and a translation of a patient structure.

10. The method of claim 8 wherein the corresponding metric in the data as pertains to the patient comprises a metric regarding at least one of a change in position of a bone in the patient, a rotation of a bone in the patient, and a translation of a bone in the patient.

11. The method of claim 1 wherein selecting a particular one of the plurality of different treatment plans as a function, as least in part, of the data as pertains to the patient to provide a selected treatment plan further comprises selecting the particular one of the plurality of different treatment plans as a function, as least in part, of both the data as pertains to the patient and information regarding results of at least one previous treatment of the treatment volume to provide a selected treatment plan.

12. The method of claim 1 wherein providing a plurality of different treatment plans for the patient comprises providing the plurality of different treatment plans well prior to the step of selecting the particular one of the plurality of different treatment plans.

13. The method of claim 1 wherein using historical information for persons other than the patient regarding physical changes over time as correspond to at least one volume within the patient comprises selecting the historical information as a function, at least in part, of identifying historical information that corresponds to at least one metric that correlates most closely to a corresponding metric in the data as pertains to the patient.

14. An apparatus to facilitate generating a treatment plan for irradiating a treatment volume within a patient, comprising:
- a first memory having stored therein a plurality of different treatment plans for the patient wherein at least one of the plurality of different treatment plans is provided by using deformation information that is obtained by at least one of:
  - using historical information for persons other than the patient regarding physical changes over time as correspond to at least one volume within the patient; and
  - using calculated information regarding physical changes as correspond to the at least one volume within the patient, wherein the calculated information comprises at least elasticity information for at least one object within the treatment volume;
- a second memory having stored therein data as pertains to the patient;
- a third memory having stored therein an original diagnostic image as pertains to the treatment volume;
- a processor operably coupled to the first memory, the second memory, and the third memory and being configured to use the deformation information to modify the original diagnostic image as pertains to the treatment volume to thereby provide at least one modified image and further having a user interface to permit a user to select a particular one of the plurality of different treatment plans as corresponds to a modified image having at least one metric that correlates most closely to a corresponding metric in the data as pertains to the patient.

15. The apparatus of claim 14 wherein at least one of the plurality of different treatment plans is provided by using the historical information for persons other than the patient regarding physical changes over time as correspond to the treatment volume and at least another of the plurality of different treatment plans is provided by using the calculated information regarding physical changes as correspond to the treatment volume.

16. The apparatus of claim 14 wherein at least one of the plurality of different treatment plans is provided by using both the historical information for persons other than the patient regarding physical changes over time as correspond to the treatment volume and the calculated information regarding physical changes as correspond to the treatment volume.

17. The apparatus of claim 14 wherein a plurality of the different treatment plans are provided by at least one of:
- using historical information for persons other than the patient regarding physical changes over time as correspond to the treatment volume; and
- using calculated information regarding physical changes as correspond to the treatment volume.

18. The apparatus of claim 14 wherein the historical information comprises information regarding changes to geometry as pertain to the at least one volume within the patient.

19. The apparatus of claim 14 wherein the historical information comprises information regarding movement of specific objects within the treatment volume.

20. A method to facilitate generating a treatment plan for irradiating a treatment volume within a patient, comprising:
- providing a treatment plan for the patient wherein the treatment plan is provided by using deformation information that is obtained by at least one of:
  - using historical information for persons other than the patient regarding physical changes over time as correspond to at least one volume within the patient; and
  - using calculated information regarding physical changes as correspond to the at least one volume within the patient, wherein the calculated information comprises at least elasticity information for at least one object within the treatment volume;
- using the treatment plan when irradiating the treatment volume within the patient.

* * * * *